(12) United States Patent
Hashimoto

(10) Patent No.: US 9,877,698 B2
(45) Date of Patent: Jan. 30, 2018

(54) ULTRASONIC DIAGNOSIS APPARATUS AND ULTRASONIC IMAGE PROCESSING APPARATUS

(75) Inventor: Shinichi Hashimoto, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 949 days.

(21) Appl. No.: 12/979,762

(22) Filed: Dec. 28, 2010

(65) Prior Publication Data

US 2011/0301462 A1    Dec. 8, 2011

(30) Foreign Application Priority Data

Jan. 13, 2010  (JP) ................................ 2010-005302
Dec. 7, 2010   (JP) ................................ 2010-272520

(51) Int. Cl.
| | |
|---|---|
| A61B 8/00 | (2006.01) |
| A61B 8/08 | (2006.01) |
| G06T 7/12 | (2017.01) |
| G06T 7/246 | (2017.01) |
| A61B 8/06 | (2006.01) |
| A61B 8/13 | (2006.01) |

(52) U.S. Cl.
CPC ............ *A61B 8/0883* (2013.01); *A61B 8/483* (2013.01); *A61B 8/52* (2013.01); *G06T 7/12* (2017.01); *G06T 7/246* (2017.01); *A61B 8/06* (2013.01); *A61B 8/13* (2013.01); *A61B 8/469* (2013.01); *A61B 8/481* (2013.01); *A61B 8/543* (2013.01); *G06T 2207/10136* (2013.01); *G06T 2207/20221* (2013.01); *G06T 2207/30048* (2013.01)

(58) Field of Classification Search
None
See application file for complete search history.

(56) References Cited

U.S. PATENT DOCUMENTS

| | | | |
|---|---|---|---|
| 2002/0072671 A1* | 6/2002 | Chenal .................. | A61B 6/463 600/450 |
| 2002/0072674 A1* | 6/2002 | Criton .................. | A61B 8/0883 600/454 |
| 2007/0255136 A1* | 11/2007 | Kristofferson et al. ....... | 600/437 |
| 2008/0077013 A1* | 3/2008 | Kawagishi et al. .......... | 600/443 |

(Continued)

FOREIGN PATENT DOCUMENTS

JP    2003-175041    6/2003

*Primary Examiner* — Amanda Lauritzen Moher
*Assistant Examiner* — Shahdeep Mohammed
(74) *Attorney, Agent, or Firm* — Oblon, McClelland, Maier & Neustadt, L.L.P.

(57) ABSTRACT

According to one embodiment, there is provided an ultrasonic diagnosis apparatus which generates a plurality of volume data over a predetermined period, executes setting of a position of at least one MPR slice relative to volume data, of the plurality of volume data, which corresponds to a first time phase, and sets positions of MPR slices corresponding to the at least one set MPR slice with respect to remaining volume data, executes segmentations of at least part of the heart into a plurality of segments, executes three-dimensional tracking processing, and optimizes the position of the MPR slice which is set in a predetermined time phase, based on the positions of the plurality of segments, and optimizes positions of the MPR slices set for the remaining volume data in association with the optimization.

12 Claims, 7 Drawing Sheets

(56) References Cited

U.S. PATENT DOCUMENTS

| | | | |
|---|---|---|---|
| 2008/0089571 A1* | 4/2008 | Kurita .................... | A61B 8/08 |
| | | | 382/131 |
| 2008/0181479 A1* | 7/2008 | Yang et al. ................ | 382/131 |
| 2008/0249414 A1* | 10/2008 | Yang et al. ................ | 600/445 |
| 2009/0074280 A1* | 3/2009 | Lu ........................... | A61B 8/00 |
| | | | 382/131 |

* cited by examiner

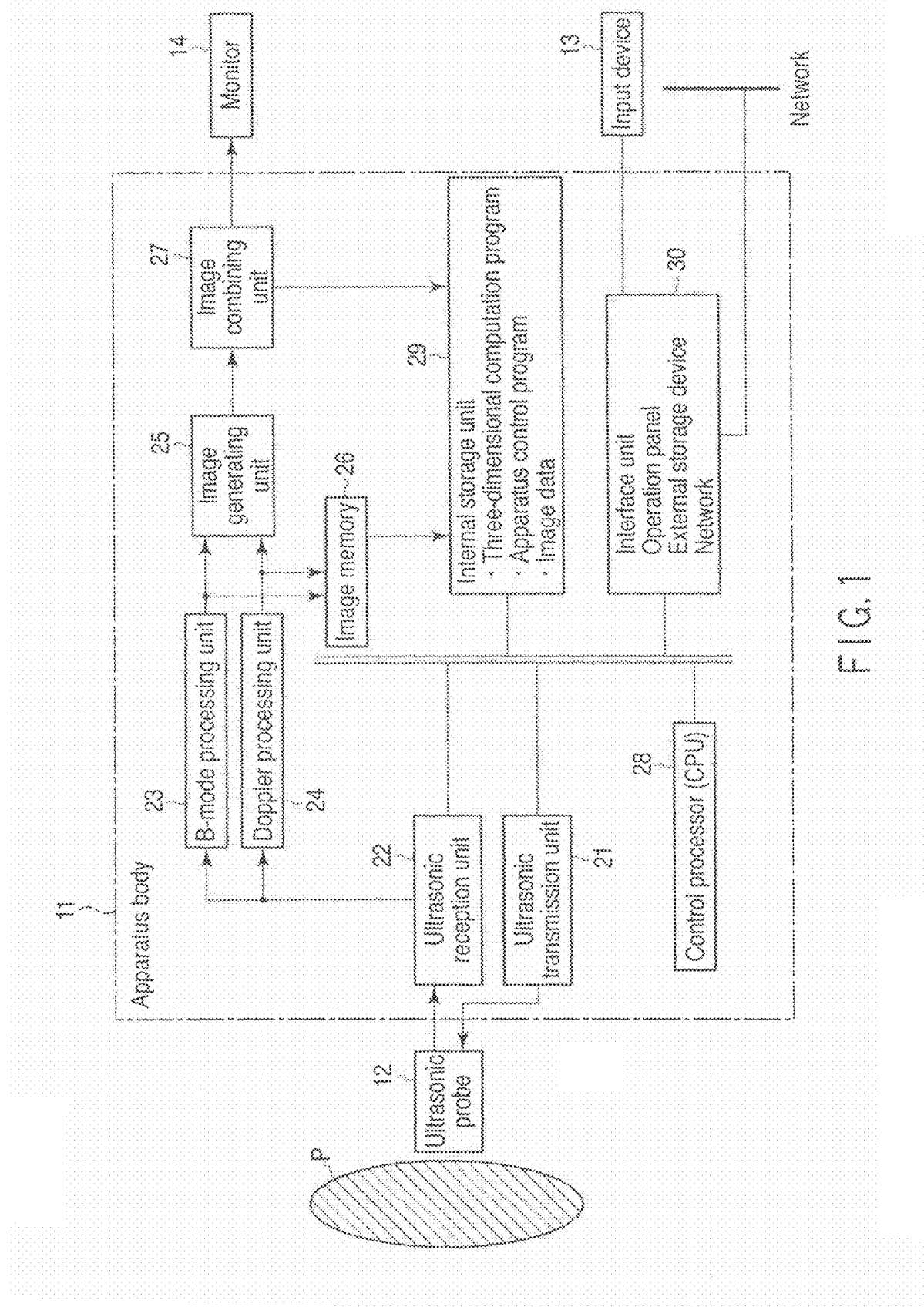
F I G. 1

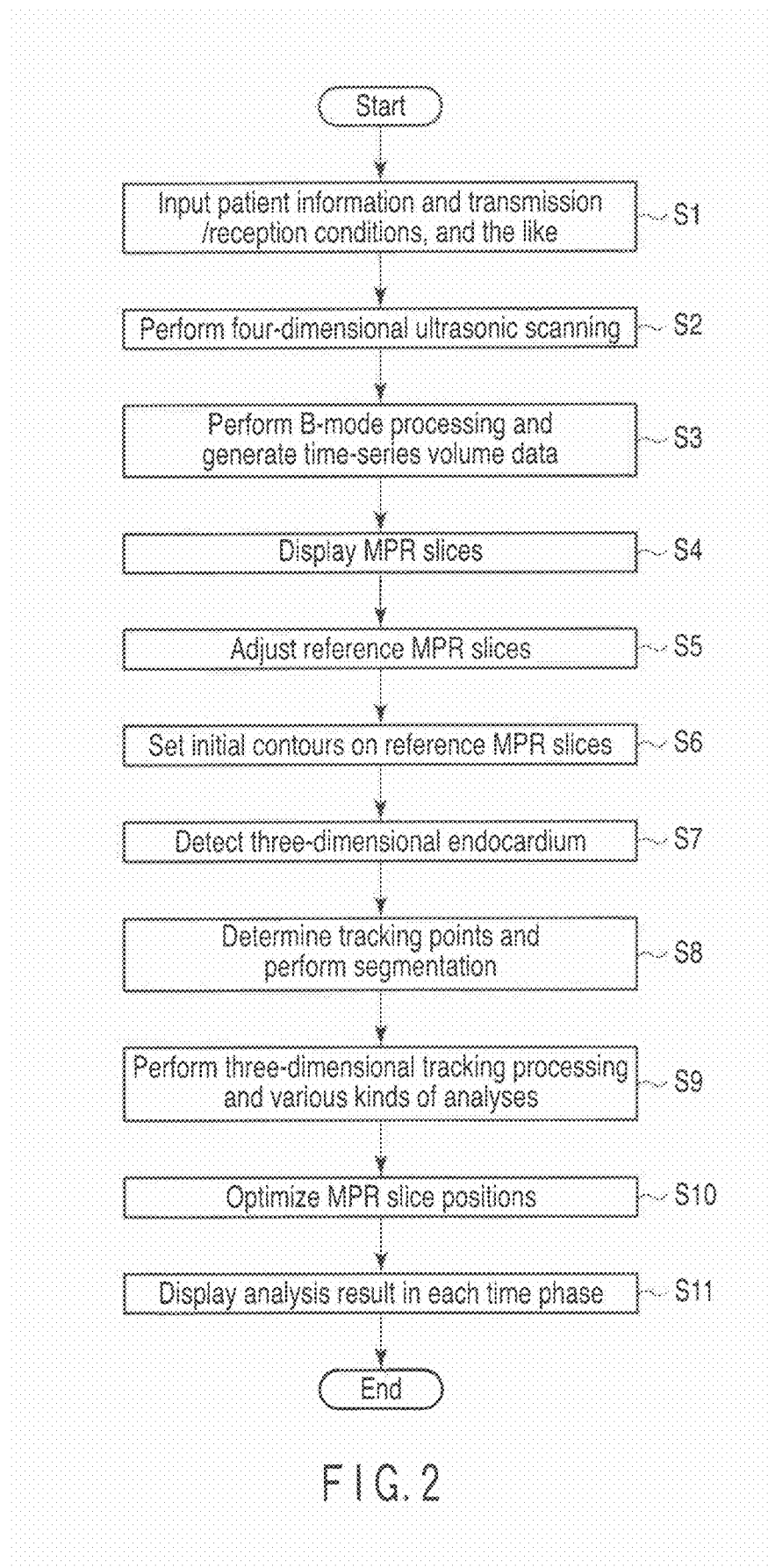
F I G. 2

4ch

Sax Apical

2ch

Sax Mild

3ch

Sax Base

ULTRASONIC DIAGNOSIS APPARATUS AND ULTRASONIC IMAGE PROCESSING APPARATUS

CROSS-REFERENCE TO RELATED APPLICATIONS

This application is based upon and claims the benefit of priority from prior Japanese Patent Applications No. 2010-005302, filed Jan. 13, 2010; and No. 2010-272520, filed Dec. 7, 2010, the entire contents of both of which are incorporated herein by reference.

FIELD

Embodiments described herein relate generally to an ultrasonic diagnosis apparatus and an ultrasonic image processing apparatus.

BACKGROUND

Ultrasonic diagnosis allows to display in real time how the heart beats or the fetus moves, by simply bringing an ultrasonic probe into contact with the body surface. This technique is highly safe, and hence allows repetitive examination. Furthermore, this system is smaller in size than other diagnosis apparatuses such as X-ray, CT, and MRI apparatuses and can be moved to the bedside to be easily and conveniently used for examination. Ultrasonic diagnostic apparatuses used in this ultrasonic diagnosis vary in type depending on the functions which they have. Some compact apparatuses which have already been developed are small enough to be carried with one hand. Ultrasonic diagnosis is free from the influences of exposure using X-rays and the like, and hence can be used in obstetric treatment, treatment at home, and the like.

Recently, an ultrasonic diagnosis apparatus has been implemented, which can acquire three-dimensional image data in real time by three-dimensionally scanning an object with ultrasonic waves and can generate and display a three-dimensional image or an arbitrary slice image. In addition, recently, a technique called three-dimensional tracking has been developed. This technique includes, first of all, inputting the initial contours (in the initial time phase) of the endocardium/epicardium of the left ventricle with respect to a plurality of MPR slices (typically, "two or more slices passing through the central cardiac chamber axis") of the heart, forming three-dimensional contours in the initial time phase from the input initial contours, sequentially tracking a local myocardial region by performing technical processing such as pattern matching for the three-dimensional contours, calculating wall motion information such as the motion vectors and strain of the cardiac muscle from the tracking result, and quantitatively evaluating the myocardial wall motion (see, for example, patent reference 1). In addition, as a technique of displaying the result obtained by three-dimensional tracking, a technique of evaluating a cardiac function for each predetermined segment such as an ASE segment has been desired and implemented. As diagnosis images to display a three-dimensional tracking result, an MPR image and a parametric image superposed on it are used from the viewpoint of recognition performance. Such images allow to observe an analysis result on a predetermined MPR slice.

When, however, the respective segments three-dimensionally arranged on MPR slices are to be displayed by the conventional technique, segment boundaries are complicated depending on the positions of the MPR slices. This makes it difficult to understand the positional relationship between the respective segments and the respective MPR slices. Assume that after initial MPR slices (typically a plane A, a plane B perpendicular to the plane A, and three planes C perpendicular to the planes A and B) are set on a 4-ch view and slices perpendicular to it by automatic MPR setting or manually, initial contours are set on the slices. In most cases, the apex point set for three-dimensional tracking processing does not exist on the initial MPR slices, and the three planes C do not match the segmentation levels of the segments.

This occurs for the following reason. Initial MPR slices are set by using images corresponding to a 4-ch view and slices perpendicular to the 4-ch view around the central left ventricle axis. In general, however, although the left ventricles have semi-ellipsoidal shapes, they are slightly bent in the longitudinal direction in most cases. For this reason, the definition of a central left ventricle axis in three-dimensional tracking processing does not strictly match the real central left ventricle axis. That is, it is not possible to uniquely define a 4-ch view, and the defined position is merely an approximate position.

When defining the initial contours of the endocardial and epicardial surfaces of the left ventricle for three-dimensional tracking on such an approximate 4-ch view and slices perpendicular to it, the conventional technique inputs the information of a base or cardiac apical position and extracts the contours of the endocardial surface by an ACT method or the like or obtains an endocardial surface by, for example, extracting a totally three-dimensional endocardial surface after tracing the endocardial surface on the initial slices. This makes it possible to obtain an epicardial surface by, for example, assuming a predetermined myocardial thickness with respect to an endocardial shape. In addition, the left ventricular myocardium is segmented into predetermined segments based on the obtained endocardial surface and the initial 4-ch view position. The central left ventricle axis can be defined as the center (area centroid or the like) of the endocardial contours (annulus region contours) of the cardiac base. The cardiac apical position can be defined as the remotest endocardial position from the center of the cardiac base. Assuming that a line connecting the cardiac apical position and the center of the cardiac base is defined as a central axis, it is possible to perform segmentation by segmenting the left ventricle at predetermined angular intervals around the central left ventricle axis with reference to the cardiac base position of the initial MPR slices.

However, the cardiac apical position in the three-dimensional endocardial surface formed in the above manner does not always exist at the initial MPR slice positions, but rather exists at a different position in most cases. This is because the initial 4-ch view MPR slice used for setting and defining initial contours and segmentation does not sometimes include the cardiac apical position in an extracted endocardial surface.

In addition, the surfaces C are set to make the initial surface C positions coincide with approximate apical, mid, and base positions when viewed from a slices perpendicular to the approximate 4-ch view described above. However, there is no guarantee that even the surfaces C set in this manner correctly match the segment positions after the above segmentation.

Furthermore, the heart undergoes shortening between an end-diastolic period and an end-systolic period. It is therefore difficult to optimize surface C positions in advance (before segmentation) so as to make them always coincide with the apical, mid, and base positions.

BRIEF DESCRIPTION OF THE DRAWINGS

FIG. 1 is a block diagram showing the arrangement of an ultrasonic diagnosis apparatus 11 according to an embodiment;

FIG. 2 is a flowchart showing a processing (MPR slice optimization processing) procedure based on the MPR slice optimization function of this embodiment;

DETAILED DESCRIPTION

Figure 3:
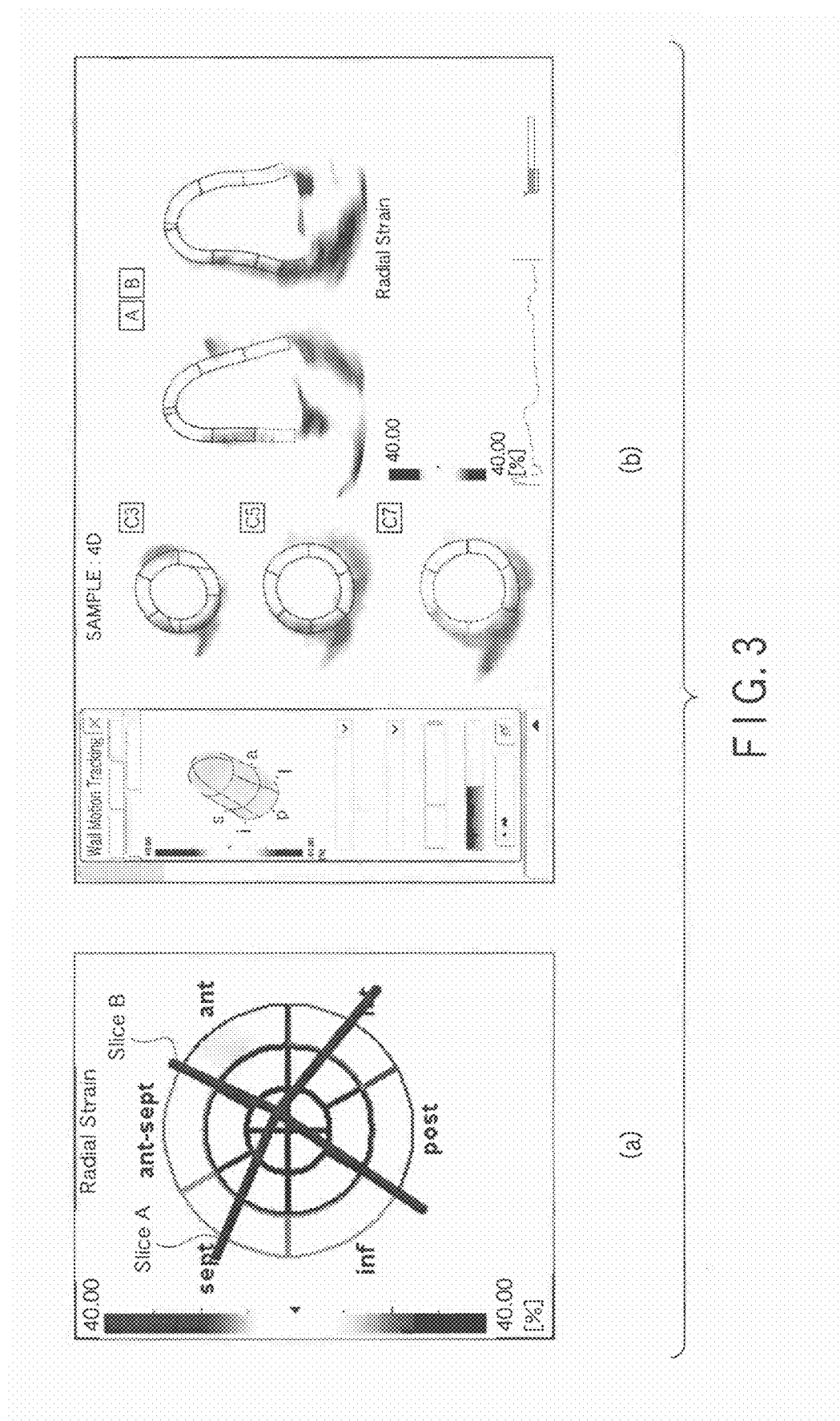
FIG. 3 is view showing, at (a) and (b), an example in which the positions of slices A and B are shifted from the cardiac apical position.

In general, according to one embodiment, there is provided an ultrasonic diagnosis apparatus comprising a signal acquisition unit configured to acquire an echo signal associated with a three-dimensional region including at least part of a heart of an object over a predetermined period by executing ultrasonic scanning on the three-dimensional region over the predetermined period, a volume data generating unit configured to generate a plurality of volume data over the predetermined period by using the echo signal associated with the three-dimensional region, a setting unit configured to execute setting processing of setting a position of at least one MPR slice relative to volume data, of the plurality of volume data, which corresponds to a first time phase, and set positions of MPR slices corresponding to the at least one set MPR slice with respect to remaining volume data in association with the setting processing, a segmentation processing unit configured to execute segmentation to segment at least part of the heart included in each of the volume data into a plurality of segments by using the at least one of the set MPR slices, a tracking processing unit configured to execute three-dimensional tracking processing by using the plurality of volume data, and an optimization unit configured to optimize the position of the MPR slice, in the plurality of volume data, which is set in a predetermined time phase, based on the positions of the plurality of segments, and optimize positions of the MPR slices set for the remaining volume data in association with the optimization.

The first embodiment of the present invention will be described below with reference to the views of the accompanying drawing. Note that the same reference numerals denote constituent elements having almost the same functions and arrangements in the following description, and a repetitive description will be made only when required.

FIG. 1 is a block diagram showing the arrangement of an ultrasonic diagnosis apparatus 11 according to this embodiment. As shown in FIG. 1, the ultrasonic diagnosis apparatus 11 includes an ultrasonic probe 12, an input device 13, a monitor 14, an ultrasonic transmission unit 21, an ultrasonic reception unit 22, a B-mode processing unit 23, a Doppler processing unit 24, an image generating unit 25, an image memory 26, an image combining unit 27, a control processor (CPU) 28, an internal storage unit 29, and an interface unit 30. The function of each constituent element will be described below.

The ultrasonic probe 12 includes a plurality of piezoelectric transducers which generate ultrasonic waves based on driving signals from the ultrasonic transmission unit 21 and convert reflected waves from an object into electrical signals, a matching layer provided for the piezoelectric transducers, and a backing member which prevents ultrasonic waves from propagating backward from the piezoelectric transducers. When the ultrasonic probe 12 transmits an ultrasonic wave to an object P, the transmitted ultrasonic wave is sequentially reflected by a discontinuity surface of acoustic impedance of internal body tissue, and is received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by a moving blood flow, cardiac wall, or the like is subjected to a frequency shift depending on the velocity component of the moving body in the ultrasonic transmission direction due to a Doppler effect.

The ultrasonic probe 12 of this ultrasonic apparatus may be a probe capable of performing ultrasonic scanning on a three-dimensional region of an object. In this case, the ultrasonic probe 12 has, for example, an arrangement to perform ultrasonic scanning on a three-dimensional region by mechanically swinging transducers along a direction perpendicular to the array direction of the transducers or an arrangement to perform ultrasonic scanning on a three-dimensional region by electrical control using two-dimensional transducers arrayed two-dimensionally. When the ultrasonic probe 12 adopts the former arrangement, the swinging circuit (swinging mechanism) performs three-dimensional scanning on the object. An examiner can therefore automatically acquire a plurality of two-dimensional tomograms by only bringing the probe body into contact with the object. It is also possible to detect the accurate distance between slices from a controlled swinging velocity. When the ultrasonic probe 12 adopts the latter arrangement, it is theoretically possible to perform ultrasonic scanning on a three-dimensional region in the same time as that required to acquire a conventional two-dimensional tomogram.

The input device 13 includes various types of switches, buttons, a trackball, a mouse, and a keyboard which are used to input, to the apparatus body 11, various types of instructions and conditions, an instruction to set a region of interest (ROI), various types of image quality condition setting instructions, and the like from an operator. When, for example, the operator operates the end button or FREEZE button of the input device 13, the transmission/reception of ultrasonic waves is terminated, and the ultrasonic diagnostic apparatus is set in a temporary stop state. When the operator issues an instruction to move the MPR slice via the input device 13, the MPR slice moves in response to the instruction. The input device 13 also includes a user interface for moving slices C1, C2, and C3 in the optimization of MPR slices (to be described later).

The monitor 14 displays morphological information (general B mode images) in the living body, blood flow information (average velocity images, variance images, power images, and the like), broadband ultrasonic images, narrowband ultrasonic images, ultrasonic images of arbitrary slices, and the like in a predetermined form based on video signals from the image generating unit 25.

The ultrasonic transmission unit 21 includes a trigger generating circuit, delay circuit, and pulser circuit (none of which are shown). The pulser circuit repeatedly generates rate pulses for the formation of transmission ultrasonic waves at a predetermined rate frequency fr Hz (period: 1/fr sec). The delay circuit gives each rate pulse the delay time required to focus ultrasonic waves into a beam for each channel and determine a transmission directivity. The trigger generating circuit applies a driving pulse to the probe 12 at the timing based on this rate pulse.

The ultrasonic transmission unit 21 has a function of instantly changing a transmission frequency, transmission driving voltage, or the like to execute a predetermined scan sequence in accordance with an instruction from the control processor 28. In particular, the function of changing a transmission driving voltage is implemented by a linear amplifier type transmission circuit capable of instantly switching its value or a mechanism of electrically switching a plurality of power supply units.

The ultrasonic reception unit 22 includes an amplifier circuit, A/D converter, and adder (none of which are shown). The amplifier circuit amplifies an echo signal received via the probe 12 for each channel. The A/D converter gives the amplified echo signals delay times necessary to determine reception directivities. The adder then performs addition processing. With this addition, the reflection component of the echo signal from the direction corresponding to the reception directivity is enhanced, and a synthetic beam for ultrasonic transmission/reception is formed in accordance with the reception directivity and transmission directivity.

The B-mode processing unit 23 receives the echo signal from the ultrasonic reception unit 22, and generates data whose signal intensity is represented by a brightness level. The B-mode processing unit 23 transmits this data to the image generating unit 25. The monitor 14 then displays the data as a B mode image representing the intensity of a reflected wave as a brightness.

The Doppler processing unit 24 frequency-analyzes velocity information from the echo signal received from the ultrasonic reception unit 22 to extract a blood flow, tissue, and contrast medium echo component by the Doppler effect, and obtains blood flow information such as an average velocity, variance, and power at multiple points.

The image generating unit 25 generally generates an ultrasonic diagnosis image as a display image by converting the scanning line signal string for ultrasonic scanning into a scanning line signal string in a general video format typified by a TV format. The image generating unit 25 also executes processing (MPR slice optimization processing) for MPR slices (to be described later) under the control of the CPU 28.

The image combining unit 27 combines the image received from the image generating unit 25 or an image memory 26 with character information of various types of parameters, scale marks, and the like, and outputs the resultant signal as a video signal to the monitor 14.

The control processor 28 has a function as an information processing apparatus (computer) and controls the operation of the main body of the this ultrasonic diagnosis apparatus. The control processor 28 reads out a dedicated program for implementing the MPR slice optimization function (to be described later) and a control program for executing a predetermined scan sequence from the internal storage unit 29, expands the programs in the memory which the processor has, and executes computation/control and the like associated with various kinds of processing.

The internal storage unit 29 stores a predetermined scan sequence for acquiring a plurality of volume data by setting different field angles, a dedicated program for implementing the MPR slice optimization function (to be described later), control programs for executing image generation and display processing, diagnosis information (patient ID, findings by doctors, and the like), a diagnosis protocol, transmission/reception conditions, a body mark generation program, and other data. This storage unit is also used to store images in the image memory 26, as needed. It is possible to transfer data in the internal storage unit 29 to an external peripheral device via the interface unit 30.

The interface unit 30 is an interface associated with the input device 13, a network, and a new external storage device (not shown). The interface unit 30 can transfer data such as ultrasonic images, analysis results, and the like obtained by this apparatus to another apparatus via a network.

(MPR Slice Optimization Function)

The MPR slice optimization function of this ultrasonic diagnosis apparatus will be described next. This function serves to optimize MPR slices when the apparatus performs, for example, three-dimensional cardiac tracking processing, by allowing to adjust the MPR slices set in volume data in a reference time phase (for example, the initial time phase) of volume data in a plurality of time phases over a period of one or more heartbeats, at an arbitrary timing, relative to the positions of the respective segments of the cardiac wall which are obtained by segmentation processing.

FIG. 2 is a flowchart showing a processing (MPR slice optimization processing) procedure based on this MPR slice optimization function. The contents of each step executed in the MPR slice optimization processing will be described with reference to FIG. 2.

[Inputting of Patient Information and Selection of Transmission/Reception Conditions and the Like: Step S1]

The operator inputs patient information and selects transmission/reception conditions (a field angle, focal position, transmission voltage, and the like), a scan sequence for ultrasonic scanning on a three-dimensional region including the heart of an object over a predetermined period, and the like via the input device 13 (step S1). The internal storage unit 29 automatically stores various kinds of input and selected information, conditions, and the like.

[Acquisition of Volume Data Over Predetermined Period: Step S2]

The control processor 28 executes real-time three-dimensional ultrasonic scanning (four-dimensional scanning) on the three-dimensional region including the heart of the object as a region to be scanned (step S2). More specifically, the control processor 28 scans, for example, a desired observation region of the heart of the object, that is, the three-dimensional region including the heart, with ultrasonic waves at a given time ti as a reference (initial time phase) by using a two-dimensional array probe or swinging probe. With this four-dimensional scanning, the control processor 28 acquires an echo signal in a time sequence (at least one heartbeat) from the three-dimensional region including the heart.

Note that four-dimensional scanning in step S2 is generally executed in synchronism with a biological signal such as an ECG. The above description about step S2 has been made on the case of sequentially repeating real-time three-dimensional ultrasonic scanning. In contrast to this, it is possible to acquire full-volume data for each time phase by segmenting the heart into a plurality of sub-volumes, acquiring data corresponding to various kinds of cardiac time phases concerning the respective sub-volumes by ultrasonic scanning on the respective sub-volumes in synchronism with a biological signal such as an ECG, and combining the acquired data posteriori.

In step S2, the control processor 28 sequentially sends each echo signal acquired in step S2 to the B-mode processing unit 23 via the ultrasonic reception unit 22. The B-mode processing unit 23 executes logarithmic amplification, envelope detection processing, and the like for each signal to generate image data whose signal intensity is expressed by a luminance level.

[Generation of Time-Series Volume Data: Step S3]

The image generating unit 25 reconstructs a plurality of time-series volume data by performing coordinate conversion for the generated time-series image data of the three-dimensional region including the heart from the real spatial coordinate system (that is, the coordinate system by which the plurality of scan slice image data are defined) into a volume data spatial coordinate system, and performing interpolation processing (step S3).

[Generation/Display of MPR Images: Step S4]

The control processor 28 automatically sets slices A, B, C1, C2, and C3 in accordance with the reference slices in a cardiac examination by using a predetermined automatic slice detection method. As an automatic slice detection method to be used, it is possible to use, for example, a technique using image pattern recognition of reference slices and pattern matching in a cardiac examination or the technique disclosed in "IEEE Conference on Computer Vision and Pattern Recognition, vol. 2, pp. 1559-1565" and the like. The image generating unit 25 generates MPR images respectively corresponding to the slices A, B, C1, C2, and C3 detected in step S4. The monitor 14 displays the generated MPR images in, for example, the form shown in FIG. 3 (step S4). The user can determine, while observing each displayed MPR image, whether the slices A, B, C1, C2, and C3 respectively match the reference slices.

Note that reference slices in a cardiac examination are slices complying with desired specifications and references, and include, for example, long-axis slices passing through a central cardiac chamber axis (a long-axis four-chamber slice (4-ch view), long-axis two-chamber slice (2-ch view), long-axis three-chamber slice (3-ch view), and the like), short-axis slices (SAXA, SAXM, and SAXB) perpendicular to the long-axis slices, and slices defined by predetermined positional relationships with the slices. Assume that the positions of the slices A, B, C1, C2, and C3 are set in volume data corresponding to each time phase.

[Adjustment of MPR Slices: Step S5]

The control processor 28 then adjusts the positions of the MPR slices in response to an instruction input from the input device 13 so as to match the MPR slices with the reference slices (step S5). That is, the user inputs the changed positions of the respective MPR slices via the input device 13 so as to make, for example, the slices A, B, C1, C2, and C3 become a 4-ch view, 2-ch view, SAXA, SAXM, and SAXB as reference slices while observing volume rendering images and MPR images generated by using volume data corresponding to a predetermined time phase (for example, an end-diastolic phase). The control processor 28 moves the respective MPR slices to the changed positions input from the input device 13. The image generating unit 25 further generates a plurality of MPR images corresponding to the plurality of MPR slices after the movement. The monitor 14 displays the respective generated MPR images in a predetermined form.

[Setting of Initial Contours on Reference MPR Slices: Step S6]

The control processor 28 sets the initial contours of the endocardial surface on reference slices (a 4-ch view and 2-ch view in this case) in response to an instruction input from the input device 13. Using, for example, the ACT method or the like allows to perform this initial setting by inputting three points per slice. However, this embodiment is not limited to this, and it is possible to perform precise input operation for each local region.

[Detection of Three-Dimensional Endocardial Surface: Step S7]

The control processor 28 then extracts a three-dimensional endocardial surface with reference to the initial contours set in step S6. The extraction algorithm to be used is not specifically limited, and any method can be used.

[Determination of Tracking Points and Segmentation: Step S8]

The control processor 28 then performs segmentation and arranges tracking points on the detected three-dimensional endocardial surface (step S8).

That is, first of all, the control processor 28 calculates the area centroid of the endocardial contours (annulus region contours) of the cardiac base, and defines it as a central left ventricle axis. Note that such a definition of the central left ventricle axis is merely an example. As another example, it is possible to define the intersection point of the 4-ch view and 2-ch view of the cardiac base as a central left ventricle axis. The control processor 28 then calculates the remotest endocardial position from the center of the cardiac base, and defines it as a cardiac apical position. The control processor 28 calculates a line connecting the center of the cardiac base and the cardiac apical position, and defines the line as a central axis. The control processor 28 also defines all the segments of the three-dimensional endocardial surface by segmenting the left ventricle at predetermined angular intervals around the central left ventricle axis with reference to the base position of the 4-ch view as the central position between the septal and lateral segments of 16 ASE segments. The control processor 28 can arrange three-dimensional tracking points on the three-dimensional endocardial surface by arranging the points at equal intervals toward the cardiac base, with the cardiac apical position being the center.

Note that it is easy to implement segmentation with another segment allocation such as allocation of 17 segments. At this point of time, it is possible to define the positional relationship between the defined positions of the segments and the positions of the 4-ch view and ch view displayed on the MPR slices A and B.

[Three-Dimensional Tracking Processing/Various Kinds of Analyses: Step S9]

The control processor 28 then calculates motion vectors by three-dimensional tracking speckle patterns of three-dimensional images in chronological order by using the set tracking points. The control processor 28 then moves the tracking points in the initial time phase by using the motion vectors, and detects the three-dimensional motion of the endocardium (or as well as of the epicardium). The control processor 28 also analyzes various kinds of quantitative parameters such as a displacement and strain by using the contour data of each frame and the like.

Note that tracking the respective tracking points is to track the three-dimensional motion of the endocardial surface (epicardial surface) of the cardiac muscle, so that the respective segments deform accordingly. In general, each segment repeatedly deforms for each cardiac cycle in such a manner that its size is maximized in each end-diastolic period and minimized in each end-systolic period. Consequently, each MPR slice defined above changes its position relative to the segment to be displayed in accordance with this deformation.

[Optimization of MPR Slice Positions: Step S10]

At the stage before optimization in step S10, as shown in, for example, FIGS. 3(a) and 3(b), the slices A and B are sometimes positioned not to pass through the cardiac apical position. In addition, the slice B is adjusted in initial setting to a position where it is perpendicular to the slice A for initial contour setting. In this case, however, the slice B is positioned near a segment boundary.

Figure 4:
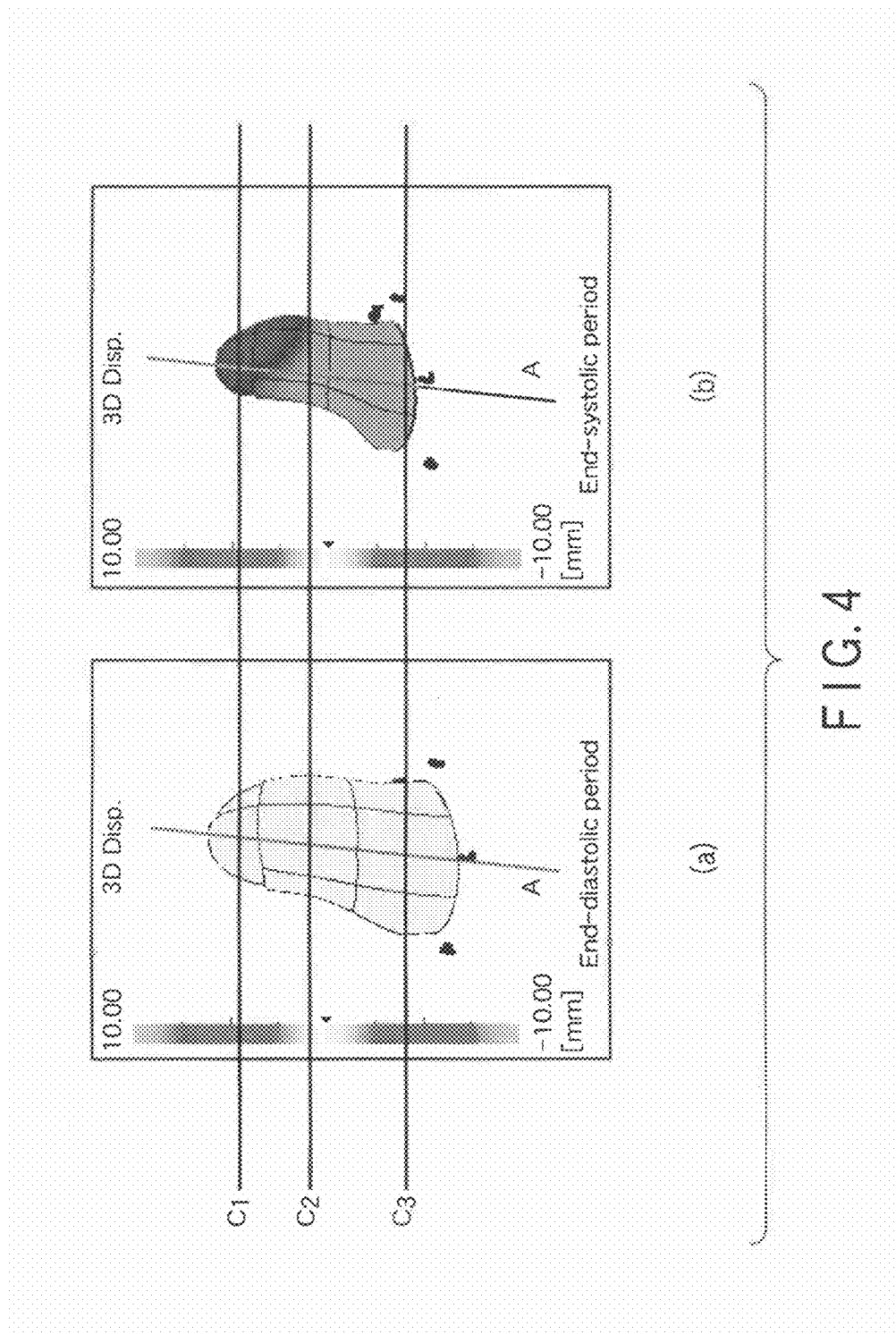
FIG. 4 is view for explaining, at (a) and (b), how the positions of slices C1, C2, and C3 set in an end-diastolic period shift outside the respective corresponding segments in an end-systolic period.

In addition, the heart generally undergoes expansion/contraction in the longitudinal direction, which is called shortening, in a cardiac cycle. For this reason, the three levels (Apical, Mid, and Base) obtained by segmentation also change. For example, the positions of the slices C1, C2, and C3 set in the initial time phase (end-diastolic period) as shown in FIG. 4(a) sometimes shift outside the respective corresponding segments in an end-systolic period as shown in FIG. 4(b).

The control processor 28 executes MPR slice position optimization processing in response to an instruction input from the input device 13 (step S10). The control processor 28 may execute the MPR slice position optimization processing automatically at a predetermined timing.

Figure 5:
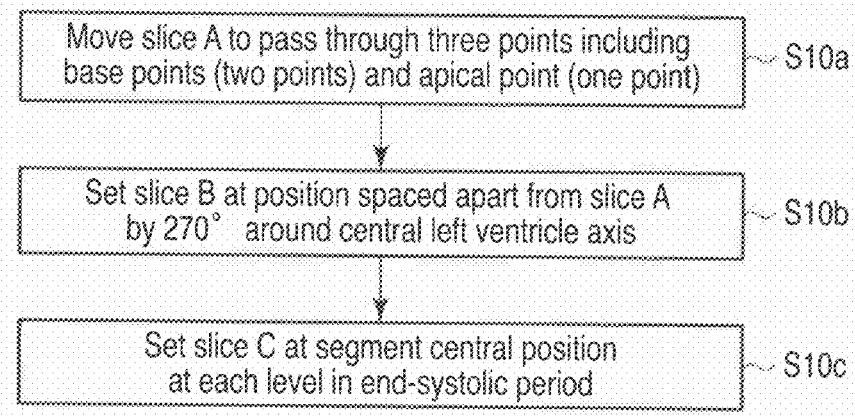
FIG. 5 is a flowchart showing a procedure for MPR slice position optimization processing.

FIG. 5 is a flowchart showing a procedure for MPR slice position optimization processing. First of all, the control processor 28 moves the slice A to a plane passing through a total of three points including the base points (two points) and an apex point (one point) (step S10a). The control processor 28 may perform this movement at the timing of receiving an instruction from the input device 13 or may automatically perform the movement at a predetermined timing using the base and apex points calculated in step S8.

Figure 6:
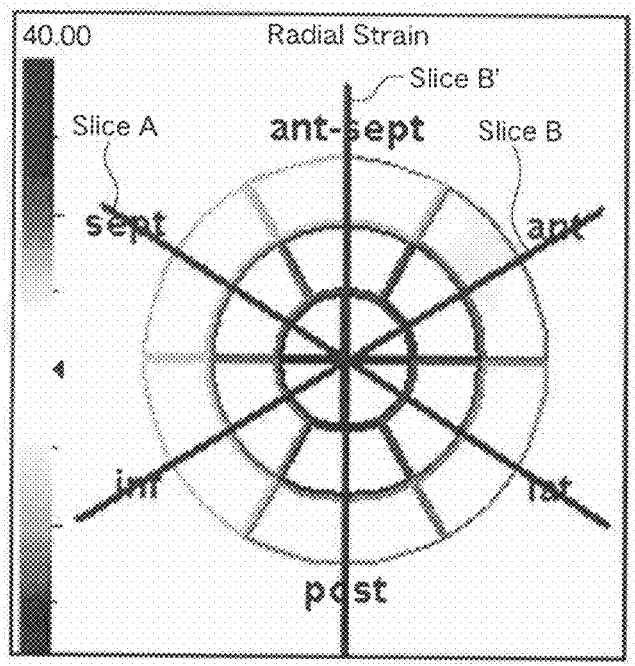
FIG. 6 is a view showing an example of the position of each of slices A, B, and B' after optimization processing.

The control processor 28 then sets the slice B at the 2-ch view position, that is, the central position between the segments on the front wall and the lower wall (step S10b). More specifically, the control processor 28 sets the slice B at the position spaced apart from the slice A by 270° around the central left ventricle axis. The control processor 28 can also set a slice B' at the 3-ch view position, as needed. In this case, the control processor 28 sets the slice B at the position spaced apart from the slice A by 60° around the central left ventricle axis. With this setting, as shown in, for example, FIG. 6, it is possible to optimize the positions of the slices A and B (or B') so as to make them pass through the corresponding segments, respectively, and intersect at the apex point.

Note that in order to reduce variations in cardiac apical position, it is more preferable to optimize the slices A and B by extracting a cardiac apical position in each time phase and setting it at the position (center of movement) where the variance is minimum.

It is generally assumed that the cardiac apical position also moves in a cardiac cycle. Therefore, the results obtained by optimizing the slices A and B in this step slightly differ from each other depending on the cardiac time phases in which optimization is executed. In this embodiment, although a cardiac time phase in which a cardiac apical position is defined is not specifically limited, assume that the slices A and B are optimized in an end-diastolic period or an end-systolic period or at a time point corresponding to 50% of a diastolic period. However, it is possible to optimize MPR slices in a time phase corresponding to an analysis result which is to be displayed or an arbitrary time phase selected by the operator, without being limited to the above time phase. Possible user interfaces in these cases may include a form of selecting a desired time phase on, for example, an ECG waveform via the input device 13 and a form of selecting a desired time phase such as "end-diastolic period", "end-systolic period", or "diastolic period" and inputting a numerical value such as "time point: 50% of" the selected period via the input device 13.

The control processor 28 then optimizes the slices C1, C2, and C3 at, for example, the segment central positions at the respective levels in an end-systolic period (step S10c). More specifically, the control processor 28 calculates the central positions of the respective segments at the respective levels (Apical, Mid, and Base) in an end-systolic time phase, and moves the slices C1, C2, and C3 so as to include the calculated central positions. The control processor 28 further sets the optimized positions of the slices A, B, C1, C2, and C3 for the volume data corresponding to the remaining time phases.

Note that a plane including the central position of each segment at each level is a curved surface instead of a flat surface according to a detailed calculation. This surface may be defined as a flat surface by selecting three points of the central points of the respective segments and calculating a flat surface including the selected three points.

Figure 7:
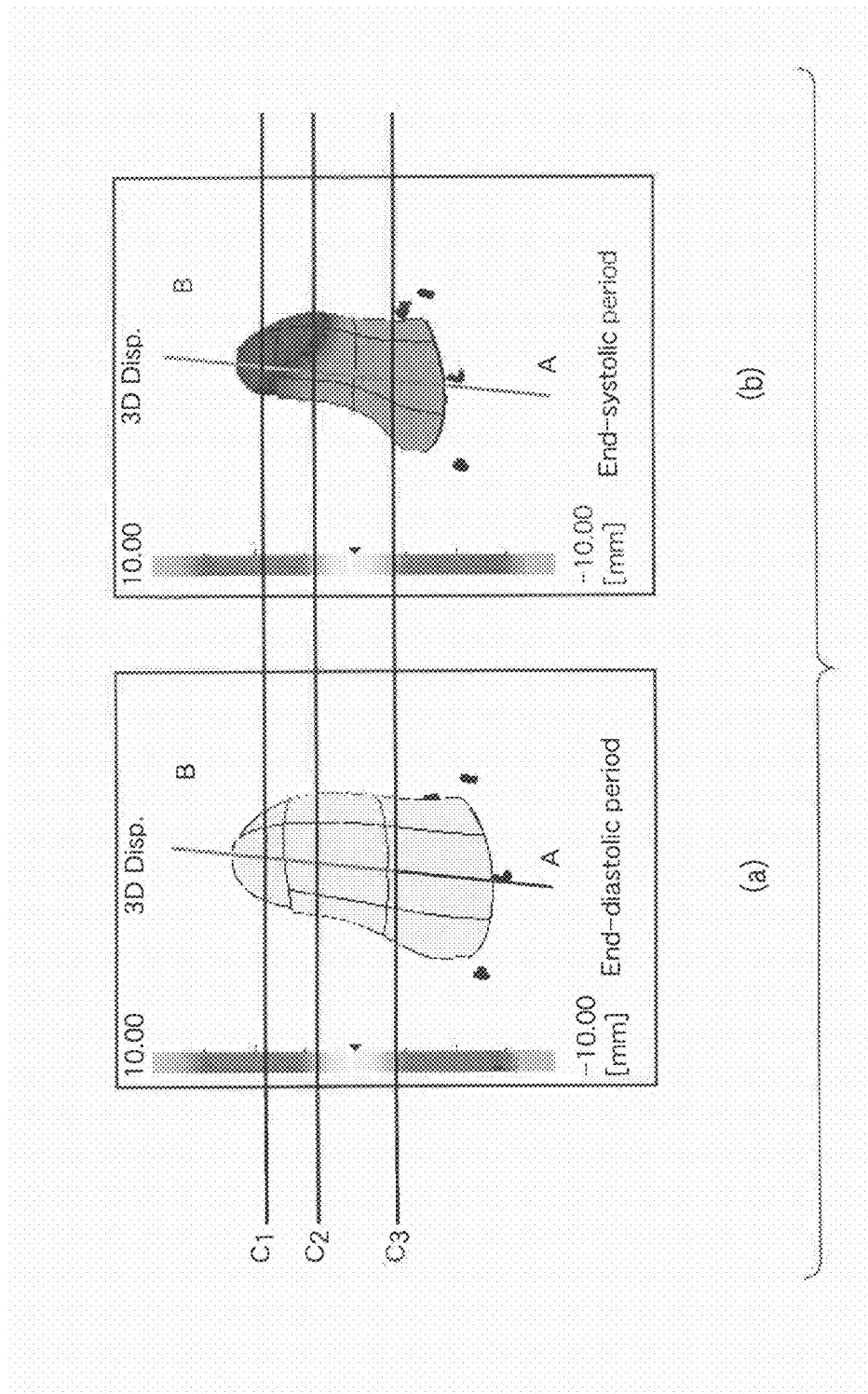
FIG. 7 is view showing, at (a) and (b), an example of the position of each of the slices C1, C2, and C3 after optimization processing in each of end-diastolic and end-systolic time phases.

The positions of slices are set in an end-systolic period in the above manner for the following reason. In an end-systolic period, the base position shifts outside the segments. It is more preferable to move the positions of the slices C1, C2, and C3 dynamically in accordance with changes within a cardiac cycle. This, however, complicates the means for implementation. It is important in this embodiment to make the slices C1, C2, and C3 keep capturing the same segment in a cardiac cycle. From this point of view, the respective slice positions are set at the central positions at the respective levels in an end-systolic period. Setting the respective positions in this manner allows the slices C1, C2, and C3 to keep capturing the same segment in either of end-diastolic and end-systolic time phases, as shown in FIGS. 7(a) and 7(b).

The use of an end-systolic period is, however, merely an example. According to another example, for example, it is possible to re-set the slices C1, C2, and C3 at the centers at the respective segment levels in predetermined time phases corresponding to an end-diastolic period and 50% of a diastolic period so as to balance the overall cardiac time phases. However, this embodiment is not limited to such time phases. It is possible to optimize MPR slices in a time phase corresponding to an analysis result which is to be displayed or an arbitrary time phase selected by the operator. It is also possible to select different time phases for the respective slices C1, C2, and C3 and adjust the positions of the slices C1, C2, and C3 in each of the selected time phases.

In the above case, the slices C1, C2, and C3 are automatically moved in a desired time phase so as to include the central positions of the respective segments. However, this embodiment is not limited to this example. For example, it is possible to move the slices C1, C2, and C3 to arbitrary positions in the respective corresponding segments by manual operation such as drag-and-drop via the input device 13. Alternatively, it is possible to input, via the input device 13, a desired condition such as "to move the slice C1 upward", "to move the slice C1 downward", or "to set the slice C1 at a position located above the bottom of the segment and corresponding to 30% of its length, when the length of the segment in the longitudinal direction is 100% (that is, to set the slice C1 based on a ratio to the segment)". The control processor 28 calculates the positions to which the respective slices should be moved, based on an input instruction, and moves the slices C1, C2, and C3 so as to make them pass through the calculated positions.

According to the above description, the control processor 28 has executed the MPR slice optimization in step S10 after the analysis processing in step S9. However, the timing of MPR slice optimization is not limited to this. For example, it is possible to execute the optimization after the segmentation processing in step S8 or execute the optimization in two steps after segmentation processing and analysis processing.

[Display of Analysis Result Obtained in Each Time Phase: Step S11]

The control processor 28 superimposes an analysis result obtained in each cardiac time phase on each MPR image corresponding to each optimized MPR slice and displays the resultant image (step S11).

(Modification)

Figure 8:
FIG. 8 shows an example of how all MPR images including 4-ch view, 2-ch view, 3-ch view, apical, mid, base images are displayed.
Figure 8:
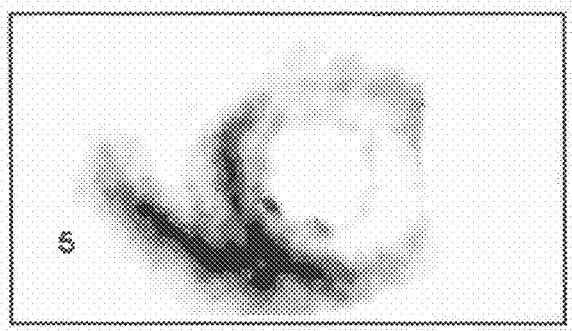
Figure 8:
Figure 8:
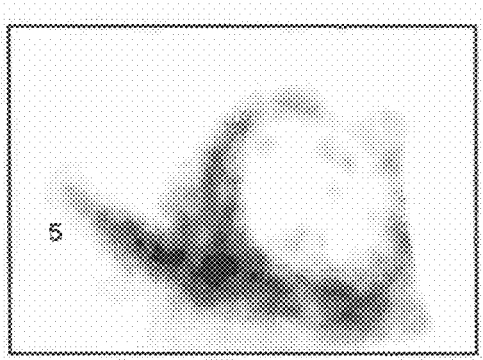
Figure 8:
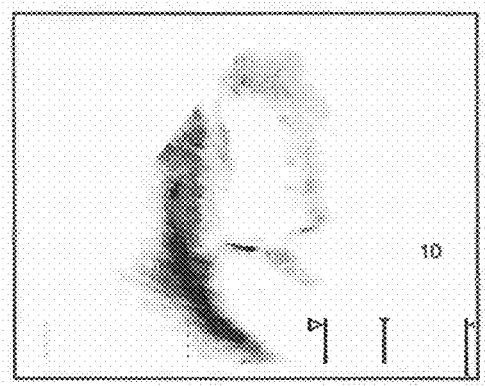
Figure 8:

The above embodiment has exemplified the case in which the slice A is set at the 4-ch view position, the slice B is set at the 2-ch view or 3-ch view position, and the slices C1, C2, and C3 are respectively set at the apical, mid, and base positions. However, it is possible to display all MPR images including 4-ch view, 2-ch view, 3-ch view, apical, mid, and base images, or to display any one of 4-ch view, 2-ch view, 3-ch view, apical, mid, and base images or MPR images corresponding to two slices C. Note that FIG. 8 shows a case in which all MPR images including 4-ch view, 2-ch view, 3-ch view, apical, mid, and base images are displayed.

(Effects)

The above arrangement can obtain the following effects.

When performing three-dimensional tracking processing by using three-dimensional image data corresponding to one or more cardiac cycle of the heart and analyzing various kinds of motion information, this ultrasonic diagnosis apparatus performs segmentation using each MPR slice on which an initial contour set before analysis and can readjust the position of each MPR slice with reference to the position of each segment obtained by segmentation. For example, therefore, this apparatus can easily and quickly optimize the positions of the respective slices so as to make the slices A and B include the cardiac apical position in an extracted endocardial surface and to properly match the slices C1, C2, and C3 with the segment positions after segmentation while keeping capturing the same segments in any time phases including an end-diastolic period and an end-systolic period.

According to this ultrasonic diagnosis apparatus, the operator need not adjust the positions of MPR slices on which analysis results after three-dimensional tracking processing are observed, for each slice, while seeing the results. Therefore, when observing analysis results on various kinds of motion information obtained by three-dimensional tracking processing upon superimposing and displaying the results on MPR images, it is possible to quickly and easily superimpose and display the analysis result for each segment on a corresponding MPR image whose position has been optimized.

Note that the present invention is not limited to the above embodiments, and constituent elements can be variously modified and embodied at the execution stage within the spirit and scope of the invention. The following are concrete modifications.

(1) Each function associated with each embodiment can also be implemented by installing programs for executing the corresponding processing in a computer such as a workstation and expanding them in a memory. In this case, the programs which can cause the computer to execute the corresponding techniques can be distributed by being stored in recording media such as magnetic disks (Floppy®) disks, hard disks, and the like), optical disks (CD-ROMs, DVDs, and the like), and semiconductor memories.

(2) The above embodiment described above has exemplified the case in which segmentation is performed for the left ventricle. Obviously, however, this embodiment is not limited to this and can be effectively applied to three-dimensional tracking processing for regions other than the left ventricle.

(3) The above embodiment described above has exemplified the case in which MPR slice optimization is applied in three-dimensional tracking processing for the heart using the ultrasonic diagnosis apparatus. However, the embodiment is not limited to three-dimensional tracking processing for the heart by using the ultrasonic diagnosis apparatus, and this MPR slice optimization function can also be applied to a case in which three-dimensional tracking processing for the heart is performed by using other medical diagnosis apparatuses such as an X-ray computed tomographic apparatus, magnetic resonance imaging apparatus, and X-ray diagnosis apparatus.

Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus comprising:
    an ultrasonic transmitter/receiver configured to acquire echo signals associated with a three-dimensional region including at least part of a heart of an object over a predetermined period by executing ultrasonic scanning on the three-dimensional region over the predetermined period;
    a computer:
        configured to generate a plurality of volume data over the predetermined period by using the echo signals associated with the three-dimensional region;
        configured to set a Multi-Planar Resolution (MPR) slice to each volume data;
        configured to segment at least part of the heart included in each of the volume data into a plurality of segments;
        configured to set a plurality of tracking points to a volume data which is one of the plurality of volume data and corresponds to a first time phase, and execute three-dimensional tracking processing concerning the plurality of tracking points by using the plurality of volume data; and
        configured to automatically adjust each position of the MPR slice set in the plurality of volume data based on a temporal change of at least one segment position among the plurality of segment positions, to obtain the MPR slice set passing an apex point and corresponding segment of the plurality of segments among the plurality of volume data, the temporal change corresponding to temporal changes of some of the plurality of tracking points acquired by the three dimensional tracking processing.

2. The apparatus according to claim 1, wherein said computer adjusts each position of the MPR slice set in the plurality of volume data, which corresponds to an end-systolic period.

3. The apparatus according to claim 1, wherein said computer adjusts each position of the MPR slice set in the plurality of volume data, which is between an end-diastolic period and an end-systolic period.

4. The apparatus according to claim 1, wherein the computer adjusts each position of the MPR slice set in the plurality of volume data, which is selected for each MPR slice when not less than two MPR slices are set in volume data corresponding to the first time phase.

5. The apparatus according to claim 1, wherein when each MPR is set in different volume data corresponding to different time phases, said computer adjusts each position of the MPR slice set in the plurality of volume data in accordance with the each set of MPR slice in different volume data.

6. The apparatus according to claim 1, wherein said computer adjusts each position of the set MPR slice set in the plurality of volume data based on a position of a structural feature point of the heart.

7. The apparatus according to claim 1, which further comprises an input circuit configured to input a changed position of the MPR slice in the volume data by manual operation, and in which
the computer adjusts each position of the MPR slice based on the input changed position.

8. The apparatus according to claim 1, which further comprises an input circuit configured to input a changed position of the MPR slice in the volume data based on a ratio to the plurality of segments, and in which
the computer adjusts each position of the MPR slice based on the input changed position.

9. The apparatus according to claim 1, which further comprises an input circuit configured to input vertical movement of the MPR slice relative to the plurality of segments in the volume data, in which
the computer adjusts each position of the MPR slice based on an input from the input circuit.

10. The ultrasonic diagnosis apparatus according to claim 1, wherein the computer repeatedly exerts adjustment at a specific time phase of a cardiac cycle.

11. The ultrasonic diagnosis apparatus according to claim 1, wherein the plurality of diagnosis regions includes at least two points set to a cardiac base and a point set to a cardiac apical position.

12. The ultrasonic diagnosis apparatus according to claim 11, wherein the cardiac apical position is set based on a variance of cardiac apical positions at a plurality of time phase.

* * * * *